United States Patent [19]

Kaplan

[11] 4,190,598
[45] Feb. 26, 1980

[54] CATALYTIC PROCESS FOR PRODUCTION OF POLYHYDRIC ALCOHOLS IN PRESENCE OF AMMONIUM CARBOXYLATES

[75] Inventor: Leonard Kaplan, Charleston, W. Va.

[73] Assignee: Union Carbide Corporation, New York, N.Y.

[21] Appl. No.: 946,314

[22] Filed: Sep. 27, 1978

[51] Int. Cl.$^2$ .................. C07C 27/06; C07C 29/16
[52] U.S. Cl. .................. 260/449 L; 260/501.2; 260/501.16
[58] Field of Search .................. 260/449 R, 449 L

[56] References Cited

U.S. PATENT DOCUMENTS 3,957,857  5/1976  Pruett et al. .................. 260/449

Primary Examiner—Howard T. Mars
Attorney, Agent, or Firm—Marylin Klosty

[57] ABSTRACT

Ammonium carboxylates having the general formula:

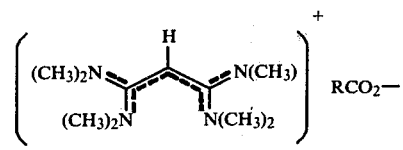

wherein R is hydrogen or a substituted or unsubstituted hydrocarbon radical. The defined carboxylates promote the formation of alkane polyols in a homogeneous liquid phase mixture wherein hydrogen and carbon monoxide are reacted in the presence of a rhodium carbonyl complex at a temperature of from about 100° C. to 375° C. and a pressure of from about 500 psia to about 50,000 psia.

7 Claims, No Drawings

CATALYTIC PROCESS FOR PRODUCTION OF POLYHYDRIC ALCOHOLS IN PRESENCE OF AMMONIUM CARBOXYLATES

This invention relates to novel ammonium carboxylates and to a process for the manufacture of alkane polyols, as well as a variety of other chemicals, such as, methanol from synthesis gas wherein such ammonium carboxylates are useful as promoters.

There are described in U.S. Pat. No. 3,833,634, issued Sept. 3, 1974 and U.S. Pat. No. 3,957,857, issued May 18, 1976, processes for reacting hydrogen and oxides of carbon in the presence of rhodium carbonyl complex catalysts. The conditions employed in those processes involve reacting a mixture of an oxide of carbon and hydrogen with a catalytic amount of rhodium in a complex combination with carbon monoxide in a homogeneous liquid phase mixture, at a temperature of between about 100° C. to about 375° C. and a pressure of between about 500 psia and about 50,000 psia. In addition to the aforementioned U.S. Patents, the following U.S. Patents and Patent application Nos. amplify the development of the process for making alkane polyols from mixtures of hydrogen and oxides of carbon:

| U.S. Pat. No. 3,878,292 | Patented April 15, 1975 |
| --- | --- |
| U.S. Pat. No. 3,878,290 | Patented April 15, 1975 |
| U.S. Pat. No. 3,878,214 | Patented April 15, 1975 |
| U.S. Pat. No. 3,886,364 | Patented May 27, 1975 |
| U.S. Pat. No. 3,940,432 | Patented February 24, 1976 |
| U.S. Pat. No. 3,929,969 | Patented December 30, 1975 |
| U.S. Pat. No. 3,952,039 | Patented April 20, 1976 |
| U.S. Pat. No. 3,948,965 | Patented April 6, 1976 |
| U.S. Pat. No. 3,944,588 | Patented March 16, 1976 |
| U.S. Pat. No. 3,957,857 | Patented May 18, 1976 |
| U.S. Pat. No. 3,968,136 | Patented July 6, 1976 |
| U.S. Pat. No. 3,974,259 | Patented August 10, 1976 |
| (formerly U.S. Ser. No. 455,380, filed March 27, 1974) | |
| U.S. Pat. No. 3,989,799 | Patented November 2, 1976 |
| (formerly U.S. Ser. No. 455,379, filed March 27, 1974) | |
| U.S. Pat. No. 4,013,700 | Patented March 22, 1977 |
| (formerly U.S. Ser. No. 526,942, filed November 25, 1974) | |
| U.S. Ser. No. 488,139 (now abandoned) | Filed July 12, 1974 |
| U.S. Ser. No. 506,862 (now abandoned) | Filed September 17, 1974 |
| U.S. Pat. No. 4,001,289 | Patented January 4, 1977 |
| (formerly U.S. Ser. No. 506,864, filed September, 17, 1974) | |
| U.S. Ser. No. 506,865 (now abandoned) | Filed September 17, 1974 |
| U.S. Ser. No. 615,093 | Filed September 19, 1975 |
| U.S. Ser. No. 537,885 (now abandoned) | Filed January 2, 1975 |
| U.S. Ser. No. 618,023 (now abandoned) | Filed September 30, 1975 |
| U.S. Ser. No. 618,061 (now abandoned) | Filed September 30, 1975 |
| U.S. Ser. No. 618,021 | Filed September 30, 1975 |
| U.S. Ser. No. 727,646 (now abandoned) | Filed September 29, 1976 |
| U.S. Pat. No. 4,111,975 | Patented September 5, 1978 |
| (formerly U.S. Ser. No. 782,986, filed March 30, 1977) | |

This invention provides 3,3-bisdimethylamino-N,N,N'N'-tetramethylacrylamidinium carboxylates as compositions having the following structural formula:

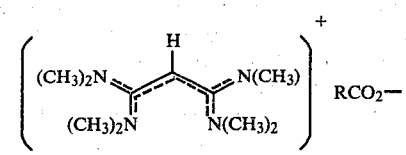

wherein R is hydrogen or a substituted or unsubstituted monovalent hydrocarbon radical.

In accordance with accepted practice, the dashed line in the formula represents a partial bond.

The hydrocarbon radicals encompassed by the invention may be linear or branched, saturated as well as unsaturated aliphatic and aromatic radicals. The nature of the hydrocarbon radical does not appear to be critical for purposes of promoting the formation of ethylene glycol in accordance with the invention.

Accordingly, R may be a linear or branched alkyl having generally from 1 to 40 carbon atoms, more usually having from 1 to 20 carbon atoms, and most often an alkyl having from 1 to 10 carbon atoms, such as, for example, methyl, ethyl, n-propyl, isopropyl, butyl octyl, dodecyl and the like; a cycloalkyl radical such as, for example, cyclopentyl and cyclohexyl; an alkenyl, such as, the vinyl group; and an aromatically unsaturated group including aryl, alkaryl and aralkyl radicals, such as, for example, phenyl, naphthyl, xylyl, tolyl, cumyl, benzyl and the like.

Among the more common R groups are hydrogen, alkyl radicals, phenyl, lower alkyl substituted aryl groups, and the aryl substituted lower alkyl groups wherein the term "lower alkyl" denotes $C_1$-$C_4$ alkyl radicals. Illustrative of such R groups are methyl, ethyl, propyl, butyl, phenyl, benzyl, phenylethyl, and the like.

Although in the usual case the hydrocarbon radicals will be unsubstituted, they may optionally be substituted with substitutents, such as, for example, halogen, hydroxyl, nitro, sulfonyl, phosphoryl, alkoxy, oxo, carbalkoxy, alkoxycarbonyl groups and the like. Examples of such carboxylates include: chloroacetate, hydroxyacetate, nitroacetate, p-methylsulfonylbenzoate $(CH_3SO_2C_6H_4COO)$, $(C_6H_5)_2P(O)CH_2CO_2^-$, ethoxypropionate, acetylbenzoate, $C_2H_5O_2CCH_2CH_2CO_2^-$ and $C_2H_5CO_2CH_2CH_2CO_2^-$.

The process of this invention involves the production of alkane polyols by reacting a mixture of hydrogen and oxides of carbon in a homogeneous liquid phase mixture containing a catalytic amount of a rhodium carbonyl complex and one or more 3,3-bisdimethylamino-N,N,N',N'-tetramethylacrylamidinium carboxylates as defined above.

The carboxylate promoter is desirably added with the initial charge of reactants in amounts of from about 0.5 to about 2.0 molecules, preferably from about 0.8 to about 1.6 molecules, and most preferably from about 0.9 to 1.4 molecules of salt for every five atoms of rhodium present in the reaction mixture.

The rhodium carbonyl complex catalysts may be in the form of rhodium carbonyl clusters or derived from a cluster form. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent by bonds directly between the metal atoms even though some non-metal atoms may be associated intimately with the cluster".

The rhodium carbonyl clusters contain rhodium bonded to rhodium or rhodium bonded to another metal, such as cobalt and/or iridium. The preferred rhodium carbonyl cluster compounds are those which contain rhodium-rhodium bonds. These compounds desirably contain carbon and oxygen in the form of carbonyl (—CO), in which the carbonyl may be "terminal", "edge-bridging", and/or "face-bridging". They may also contain hydrogen and carbon in forms other than carbonyl. The structure of two distinct rhodium carbonyl clusters having the respective empirical formulas $Rh_6(CO)_{16}$ and $[Rh_{12}(CO)_{30}]^{2-}$, and which are suitable for use in this invention, are shown for example in U.S. Pat. No. 3,957,857.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promotor of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp299-302, June (1969).

A number of nitrogen and/or oxygen-containing bases may be used in the process of the present invention. For the purposes of this invention, the bases can be considered to promote the activity of the rhodium catalysts.

Nitrogen Lewis bases used as promotors generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N═), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

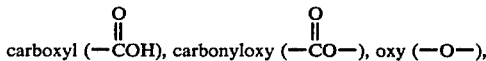

-continued

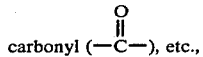

all of said groups containing Lewis base oxygen atoms. In this respect, it is the "hydroxyl" oxygen in the

and and "oxy" oxygen in the

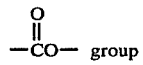

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypryidine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine, picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines and promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylenetetraamine, and the like. In addition any compounds capable of yielding an amino nitrogen under the reaction conditions of the present invention are promoters, as in the case of an amide, such as formamide, cyanamide, and urea, or an oxime. Further illustrative of Lewis base nitrogen compounds are aliphatic such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine; quinoline; substituted quinolines, 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2'-dipyridyl; ethyl-substituted 2,2'-dipyridyl; 4-triethylsilyl-2,2'-dipyridyl; 1,4-diazabicyclo [2.2.2] octane, methyl substituted 1,4-diazabicyclo [2.2.2] octane, purine and the like.

Also included herein are the use of dimorpholine compounds characterized by the formula:

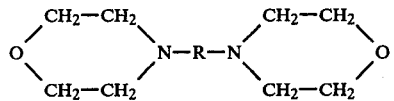

wherein R is divalent alkylene of 1 to about 30 carbon atoms and 1,4-phenylene.

The base provided to the reaction mixture is present in an amount which is equal to or greater than that amount, determined from the bases basicity, which achieves the optimum rate of formation of said alkane polyol at said correlated catalyst concentration, temperature and pressure of such reaction mixture.

The concentration of the base will typically be within about 0.001 to about 10 molar. Obviously this range is definitive of the potential scatter of concentrations predicated on the varieties of the basicities of the bases available.

Under reaction conditions the base is preferably used in amounts from about 0.02 to about 40 equivalents of base, most preferably from about 0.1 to about 20 equivalents base, for every atom of rhodium in the reaction mixture. The number of equivalents of base is equal to the number of molecules of base times the number of nitrogen atoms in each molecule.

In practicing the method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The process is suitably effected over a wide superatmospheric pressure range of from about 500 psia to about 50,000 psia. Pressures as high as 50,000 psia, and higher can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8000 psia, results in cost advantages which are associated with low pressure equipment requirements. In attempting to foresee a commercial operation of this process, pressures between about 4,000 psi and 16,000 psia appear to represent most realistic values.

Illustrative solvents which are generally suitable in making the homogeneous mixture include, for example, ethers such as tetrahydrofuran, tetrahydropyran, diethyl ether, 1,2-dimethoxybenzene, 1,2-diethoxybenzene, and mono- and dialkyl ethers of ethylene glycol, of propylene glycol, of butylene glycol, of diethylene glycol, of butylene glycol, of diethylene glycol, of dipropylene glycol, of triethylene glycol, of tetraethylene glycol, of dibutylene glycol, of oxyethylenepropylene glycol, etc; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate etc.; water; gamma-butyrolactone, deltavalerolactone; substituted and unsubstituted tetrahydrothiophene-1,1-dioxides (sulfolanes) as disclosed in U.S. application Ser. No. 537,885, filed on Jan. 2, 1975. These include sulfolanes of the formula:

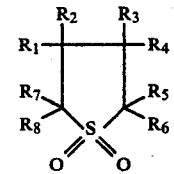

wherein each of $R_1$ through $R_8$ is at least one of hydrogen; hydroxyl; straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkyl-aryl, or aralkyl group such as phenyl, naphthyl, xylyl, tolyl, benzyl, beta-phenylethyl and the like; and ether of the formula $(O-R°)$ wherein $R°$ may be aryl or lower alkyl having from 1 to 12 carbon atoms, preferably 1 to 4 carbon atoms in the alkyl chain; an alkylene or polyalkylene ether of the formula $-(OC_nH_{2n})_x-OR°°$ wherein n has an average value of from 1 to about 4, x has an average value of from 1 to about 150, preferably 1 to about 20, most preferably 1 to about 4, and $R°°$ may be hydrogen or alkyl having from 1 to 6 carbon atoms in the alkyl chain, such as poly(oxyethylene), poly(oxyethylene-oxypropylene), alkylene and polyalkylene glycols and lower alkyl ethers thereof; a carboxylate group of the formula:

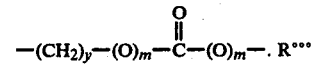

wherein y may have value between 0 and 12, m and m° may be zero or one provided that when either m or m° is one the other is zero, and $R°°°$ may be a lower alkyl group having from 1 to 12 carbon atoms, preferably from 1 to 4 carbon atoms, or aryl, and the like.

Also, the crown ethers are suitable herein, particularly those as described in U.S. Patent Application Ser. No. 832,384 filed Sept. 13, 1977, now U.S. Pat. No. 4,162,261, issued July 24, 1979 which is incorporated by reference herein.

The crown ethers contain in the principal ring at least 4 oxygen atoms each separated from the other by at least two aliphatic carbon atoms in series. The principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or mixtures of them. The maximum number of ring oxygen atoms in the principal ring may be as much as about 100, however, it is desirable that those ring oxygen atoms joined to groups other than ethylene or substituted ethylene number not more than about 50 when the number of such ring oxygen atoms exceeds about 52.

These crown ethers include [18]-crown-6 and [15]-crown-5.

Also suitable as solvents for use in the invention are phosphine oxide compounds which include a single phosphoryl groups, and the remaining atoms bonded to the phosphorous are carbon which may be substituted by at least another carbon atom, hydrogen, fluorine and/or oxygen. The phosphine oxide compounds should be free of sulfur atoms and halogen atoms except fluorine. Such compounds are more fully described in Ser. No. 920,828, filed June 30, 1978, the disclosure of which is incorporated herein by reference.

The preferred solvents for practising the invention are a number of solvents which have heretofore been described in the production of alkane polyols from synthesis gas.

Particularly desirable solvents for tetraglyme, sulfolane, gamma-butyrolactone and the crown ethers. Other very desirable solvents include mixtures of tetraglyme and sulfolane, mixtures of sulfolane and butyrolactone, mixtures of crown ethers and sulfolane, mixtures of crown ethers and tetraglyme, mixtures of crown ethers and butyrolactone, mixtures of tetraglyme and butyrolactone and mixtures of phosphine oxides with one or more of tetraglyme, sulfolane, butyrolactone and crown ethers.

The temperature which may be employed can vary over a wide range of elevated temperatures. In general, the process can be conducted at a temperature in the range of from about 100° C. and upwards to approximately 375° C., and higher. Temperatures outside this stated range are not excluded from the scope of the invention. At the lower end of the temperature range, and lower, the rate of reaction to desired product becomes markedly slow. At the upper temperature range, and beyond, signs of some catalyst instability are noted. Notwithstanding this factor, reaction continues and alkane polyols and/or their derivatives are produced. Additionally, one should take notice of the equilibrium reaction for forming ethylene glycol

2CO+3H$_2$⇌HOCH$_2$CH$_2$OH

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher pressures, however, do not represent preferred embodiments of the invention in view of the high investment costs associated with erecting chemical plants which utilize high pressure utilities and the necessity of fabricating equipment capable of withstanding such enormous pressures. However, such high pressures may prove to be justified economically because of high rates of glycol production and enhanced retention of rhodium in solution. Suitable temperatures are between about 150° C. to about 350° C., and desirably from about 210° C. to about 320° C.

The process is effected for a period of time sufficient to produce the alkane polyols and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressures exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of CO:H$_2$ is in the range of from about 20:1 to about 1:20, suitably from about 10:1 to about 1:10 and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or solvents, can be recycled to the reaction zone, if desired. All or a portion of such fraction can be removed for recovery of the rhodium values or regeneration to the active catalyst and can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium (II) propionate, rhodium(II) butyrate, rhodium(II) valerate, rhodium(II) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857 the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such of formed in the reaction.

EXAMPLE 1

3,3-Bisdimethylamino-N,N,N',N'-tetramethylacrylamidinium benzoate was prepared as follows:

A solution of 2.11 g (8.3 mmoles) of cesium benzoate in 45 ml of ethanol (dried over molecular sieves) was added to a slurry of 2.6 g (8.3 mmoles) of 3,3-bisdimethylamino-N,N,N',N'-tetramethylacrylamidinium perchlorate[1] in 45 ml of dry ethanol. The resulting mixture was stirred overnight, filtered, and the filtrate evaporated to dryness at 35° C. To the residue dissolved in 10 ml of dry ethanol was added an additional 0.97 g of the perchlorate. The resulting mixture was stirred overnight, filtered, and the filtrate evaporated to dryness at 35° to yield 2.0 g of product, isolated as the hemihydrate.

Anal. Found: C, 62.43; H, 8.88; N, 15.64. Calcd. for $C_{18}H_{30}N_4O_2 \cdot \frac{1}{2}H_2O$: C, 62.94; H, 9.10; N, 16.31. Nmr (acetone-$d_6$): $\tau = 1.8$-2.9 (m, 5H), 6.22 (s, 1.1H), 7.00 (s, 24H).

(1)Z. Janousek, Dissertation, University of Louvain, Belgium, 1972.

Other 3,3-bisdimethylamino-N,N,N',N'-tetramethylacrylamidinium carboxylates in accordance with the invention may be conveniently prepared by the procedure of Example 1 by anion exchange of the percholrate with a suitable salt of the corresponding carboxylic acid. The carboxylates thus formed are effective promoters of ethylene glycol production when used, for example, in accordance with the procedure of Examples 2-8.

In the examples set forth in the Table below, the following procedure was employed:

A 150 ml. capacity stainless steel reactor capable of withstanding pressures up to 7,000 atmospheres was charged with a premix of 75 cubic centimeters (cc) of tetraglyme, 3 millimoles (mmol) of rhodium in the form of rhodium dicarbonylacetylacetonate, specified amounts of 3,3-Bisdimethylamino-N,N',N'-tetramethylacryl-amidinium benzoate, and a co-promoter (where indicated). The reactor was sealed and charged with a gaseous mixture containing equal molar amounts of carbon monoxide and hydrogen to a pressure of 8000 psig. Heat was applied to the reactor and its contents; when the temperature of the mixture inside the reactor reached 220° C., as measured by a suitably placed thermocouple, an additional adjustment of carbon monoxide and hydrogen ($H_2$:CO = 1:1 mole ratio) was made to bring the pressure back to 8000 psig. The temperatures set forth in the Table were maintained at the desired value for 4 hours.

After the reaction was terminated, the vessel and its contents were cooled to room temperature, the excess gas vented and the reaction product mixture was removed. Analysis of the reaction product mixture was made by gas chromatographic analysis using a Hewlett Packard FM TM model 810 Research Chromatograph.

The product weights (in grams) of ethylene glycol and methanol as determined from the analysis of the product mixture is shown in the Table, as well as the rhodium recovery based on the total rhodium charged to the reactor.

Rhodium recovery was determined by atomic absorption analysis of the contents of the reactor after the venting of the unreacted gases at the end of the reaction. The rhodium recovery values recited below are the percent rhodium based on the total rhodium charged to the reactor that is soluble or suspended in the reaction mixture.

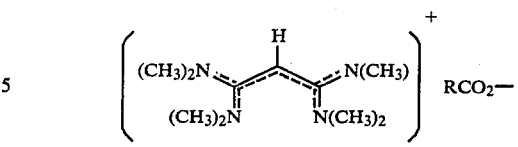

wherein R is hydrogen, an unsubstituted monovalent

TABLE

| | | 3,3-Bisdimethylamino-N,N,N',N'-Tetramethylacrylamidinium Benzoate as Promoter for Production of Ethylene Glycol | | | | |
|---|---|---|---|---|---|---|
| Examples | mmoles of Promoter | Co-promoter, mmoles | Temperature | Methanol, g | Ethylene Glycol, g | % Rh Recovered |
| 2 | 0.65 | — | 220° C. | 1.53 | 3.82 | 83 |
| 3 | 0.75 | — | 220 | 1.39 | 3.41 | 88 |
| 4 | 0.65 | — | 240 | 2.56 | 5.14 | 46 |
| 5 | 0.75 | — | 240 | 2.71 | 5.39 | 57 |
| 6 | 0.65 | Pyridine, 1.25 | 220 | 2.05 | 3.05 | 90 |
| 7 | 0.75 | Pyridine, 1.25 | 220 | 1.93 | 3.11 | 94 |
| 8 | 0.75 | Pyridine, 1.25 | 240 | 3.45 | 3.77 | 53 | hydrocarbon radical or a substituted monovalent hydrocarbon radical where the substituent is halogen, hydroxyl, nitro, sulfonyl, phosphoryl, alkoxy, oxo, carbalkoxy or alkoxycarbonyl.

2. The process of claim 1 wherein the temperature of the reaction is from about 210° C. to about 320° C.

3. The process of claim 1 wherein the pressure of the reaction is from about 4,000 psia to about 16,000 psia.

4. The process of claim 1 wherein the reaction is effected in the presence of an organic solvent.

5. The process of claim 1 wherein the ammonium carboxylate is 3,3-bisdimethylamino-N,N,N',N'-tetramethylacrylamidinium benzoate.

6. The process of claim 4 wherein the solvent is tetraglyme.

7. The process of claim 4 wherein the solvent is sulfolane.

What is claimed is:

1. The process for producing alkane polyols in a homogeneous liquid phase mixture which comprises reacting hydrogen and an oxide of carbon in the presence of a rhodium carbonyl complex and an ammonium carboxylate at a pressure of from about 500 psia to about 50,000 psia and a temperature of from about 100° C. to about 375° C. sufficient to produce said alkane polyols, wherein said ammonium carboxylate has the general formula:

* * * * *

UNITED STATES PATENT AND TRADEMARK OFFICE
CERTIFICATE OF CORRECTION

PATENT NO. : 4,190,598
DATED : February 26, 1980
INVENTOR(S) : Leonard Kaplan

It is certified that error appears in the above-identified patent and that said Letters Patent are hereby corrected as shown below:

Column 9, line 33, "rhodium (II)" should read -- rhodium (III) --- .

Signed and Sealed this

Eleventh Day of November 1980

[SEAL]

Attest:

SIDNEY A. DIAMOND

Attesting Officer

Commissioner of Patents and Trademarks